United States Patent [19]
Chen et al.

[11] Patent Number: 6,005,097
[45] Date of Patent: Dec. 21, 1999

[54] PROCESSES FOR HIGH-YIELD DIASTEREOSELECTIVE SYNTHESIS OF DIDEOXYNUCLEOSIDES

[75] Inventors: Shu-Hui Chen, Hamden; Xiuyan Li, New Haven, both of Conn.

[73] Assignee: Vion Pharmaceuticals, Inc., New Haven, Conn.

[21] Appl. No.: 08/663,674

[22] Filed: Jun. 14, 1996

[51] Int. Cl.$^6$ .................................................. C07H 19/04
[52] U.S. Cl. .................................. 536/27.11; 536/27.14; 536/28.2
[58] Field of Search .......................................... 536/27.11

[56] References Cited

U.S. PATENT DOCUMENTS 5,175,267  12/1992  Chu ...................................... 536/27.11

FOREIGN PATENT DOCUMENTS

92/20696  11/1992  WIPO .
94/10186   5/1994  WIPO .
95/07086   3/1995  WIPO .
95/07287   3/1995  WIPO .

OTHER PUBLICATIONS

Beach et al., "Highly Stereoselective Synthesis of Anti–HIV 2', 3'–Dideoxy–and 2', 3'–Dideoxy–2', 3'–didehydronucleosides," *J. Organic Chem.*, 57(14), 3887–3894 (Jul. 3, 1992).

Hanessian et al., "Mild and Efficient Preparation of γ–Substituted α, β–Unsaturated γ–Butyrolactones from Epoxides," *J. Chem. Soc., Chem. Comm.*, (10), 754–755 (May 15, 1986).

Figueredo et al., "Studies on Structurally Simple α, β–Butenolides. VII. An Easy Entry to γ–Thiomethyl–and γ–Aminoethyl–α,β–butenolides," *Tetrahedron*, 43(8), 1881–1886 (1987).

Reich et al., "Organoselenium Chemistry, Conversion of Ketones to Enoles by Selenoxide Syn Elimination," *J. Am. Chem. Soc.*, 97(19), 5434–5447 (Sep. 17, 1975).

Balzarini, J.; Kang, G.J.; Dalal, M.; Herdewijin, P.; De Clercq, E.; Broder, S.; Johns, D.G.; *Mol. Pharmacol.* 1987, 32, 162–167.

Yarchoan, R.; Mitsuya, H.; Thomas, R.V.; Pluda, J.M.; Hartman, N.R.; Perno, C–F.; Marczyk, K.S.; Allain, J–P.; Johns, D.G.; Broder, S.; *Science* (Washington, D.C.) 1989, 245, 412–415 (Jul. 28, 1989).

Mitsuya, H.; Broder, S.; *Proc. Natl. Acad. Sci. U.S.A.* 1986, 83, 1911–1915 (Mar.).

Mansuri, M.M.; Starrett, J.E.; Ghazzouli, I.; Hitchcock, M.J.M.; Sterzycki, R.Z.; Brankovan, V.; Lin, T.S.; August, E.M.; Prusoff, W.H.; Sommadossi, J–P.; Martin, J.C.; *J. Med. Chem.* 1989, 32, 461–466 (Issue No. 2).

Chang, C–N.; Doong, S–L.; Zhou, J.H.; Beach, J.W.; Jeong, L.S.; Chu, C.K.; Tasi, C–H.; Cheng, Y–C.; *J. Biol. Chem.* 1992, 267, 13938–13942(Issue No. 20, Jul. 15, 1992).

Doong, S–L.; Tasi, C–H.; Schinazi, R.F.; Liotta, D.C.; Cheng, Y–C.; *Proc. Natl. Acad. Sci. U.S.A.* 1991, 88, 8495–8499 (Oct.).

Lin, T–S.; Luo, M–Z.; Lin, M–C.; *Tetrahedron Lett.* 1994, 35, 3477–3480 (No. 21).

Lin, T–S.; Luo, M–Z.; Liu, M–C.; Pai, S.B.; Dutschman, G.E.; Cheng, Y C.; *J. Med. Chem.* 1994, 37, 798–803 (Issue No. 6).

Lin, T–S.; Luo, M–Z.; Liu, M–C.; Zhu, Y–L.; Gullen, E.; Dutschman, G.E.; Cheng, Y–C.; *J. Med. Chem.* 1996, 39, 1757–1759 (Issue No. 9).

Chu, C.K.; Babu, J.R.; Beach, J.W.; Ahn, S.K.; Huang, H.; Jeong, L.S.; Lee, S.J.; *J. Org. Chem.* 1990, 55, 1418–1420 (issue No. 5).

Wilson, L.J.; Liotta, D.; *Tetrahedron Lett.* 1990, 31, 1815–1818 (Issue No. 13).

Wilson, L.J.; Liotta, D.; *J. Org. Chem.* 1992, 57, 1948–1950 (Issue No. 7).

Young, R.J.; Shaw–Ponter, S.; Thomson, J.B.; Miller, J.A.; Cumming, J.G.; Pugh, A.W.; Rider, P.; *Bioorg. Med. Chem. Lett.* 1995, 5, 2599–2604 (issue No. 22).

Ryu, I.; Murai, S.; Niwa, I; Sonoda, N.; *Synthesis* 1977, 874–876.

Fujimori, S.; Iwanami, N.; Hashimoto, Y.; Shudo, Ko.; *Nucleosides and Nucleotides* 1992, 11, 341–349 (Issue No. 2–4).

Tanigughi, M.; Koga, K.; Yamada, S.; *Tetrahedron* 1974, 30, 3547—3552).

Kim, C.; Marquez, V.E.; Broder, S.; Mitsuya, H.; Driscoll, J.S.; *J. Med. Chem.* 1987, 30, 862—866 (Issue No. 5).

*Primary Examiner*—John Kight
*Assistant Examiner*—L. Eric Crane
*Attorney, Agent, or Firm*—Henry D. Coleman; R. Neil Sudol

[57] ABSTRACT

The present invention relates to methods for substantially enhancing the stereoselective synthesis of β-anomeric nucleoside analogs. In methods according to the present invention, the introduction of a phenylseleno group onto a blocked lactone sugar precursor may be selected so that the desirable phenylseleno substituent is introduced on the side of the blocked lactone away from the blocking group. This stereospecific introduction of the phenylseleno group in sugar precursor allows the synthesis of nucleoside analogs and in particular, 2',3',-dideoxy- and 2',3'-dideoxy-2',3'-didehydronucleoside analogs in very high yield. In certain preferred embodiments, the preferred phenylseleno blocked lactone is obtained in an amount representing approximately 90% or more of the total amount of the stereoisomers obtained. In even more preferred embodiments, the amount of the preferred stereoisomer is at least 95%, even more preferably at least about 97% of the total amount of phenylseleno blocked lactone produced.

19 Claims, 1 Drawing Sheet

PROCESSES FOR HIGH-YIELD DIASTEREOSELECTIVE SYNTHESIS OF DIDEOXYNUCLEOSIDES

FIELD OF THE INVENTION

The present invention relates to diastereoselective processes for preparing optically active cis-nucleosides and nucleoside analogs and derivatives. The novel processes of this invention allow the stereo-controlled synthesis of a given enantiomer of a desired cis-nucleoside or nucleoside analog or derivative in high optical purity and with high yield. This invention also relates to the production of intermediates useful in the process of this invention.

BACKGROUND OF THE INVENTION

The emergence of 3'-azido-3'-deoxythymidine (AZT) as an anti-HIV agent has demonstrated the biological importance of nucleosides missing a 3'-hydrol group. Moreover, the discovery that 2',3'-dideoxy (dd) and 2',3'-didehydro-2', 3'-dideoxy (D4) nucleoside analogs exhibit potent antiviral activity has spurred both the search for superior therapeutic agents and the development of high-yielding process for the synthesis of such nucleosides. See, for example, De Clercq, E. J. *Chemother.*, Supp. A 1989, 23, 35.; Balzarini, et al., *Mol. Pharmacol.* 1987, 32, 162.

As the result of systematic modifications at both the sugar and base moieties, a number of 2',3'-dideoxynucleoside derivatives have been approved for clinical use against viral infection. These include D-β-ddI (2',3'-dideoxyinosine), D-β-ddC (2',3'-dideoxycytidine, Mitsuya and Broder, *S. Proc. Natl. Acad. Sci. U.S.A.* 1986, 83, 1911) and D-β-D4T (2',3'-didehydro-2',3'-dideoxythymidine, Mansuri, et al., *J. Med Chem.* 1989, 32, 461). Recently, a number of the L-configuration nucleoside analogs, the enantiomers of the natural D-nucleosides, have emerged as potent antiviral agents against HBV and HIV. These analogs include (–)SddC (3TC) [(2-hydroxymethyl-1,3-oxathiolan-4-yl) cytosine]; (–)FSddC (-FTC) [(2-hydroxymethyl-1,3-oxathiolan-4-yl)-5-fluorocytosine, Chang, C-N., et al., *J. Biol. Chem.*, 1992, 267, 13938–13942 and Doong, S-L. Et al., *Proc. Natl. Acad. Sci. U.S.A.* 1991, 88, 8495–8499]; β-L-ddC (β-L-2',3'-dideoxycytidine, Lin, T-S., et al., *Tetrahedron Lett.* 1994, 35, 3477 and Lin, T-S., et al., *J. Med. Chem.* 1994, 37, 798–803); β-L-FddC (β-L-3-L-5-Fluoro-2',3'-dideoxycytidine, Lin, T-S., et al., *J. Med. Chem.* 1994, 37, 798–803); and β-L-FD4C (β-L-5-fluoro-2',3'-dideoxy-2',3'-didehydrocytidine, Lin, T-S. et al., *J. Med. Chem.* 1996, 39, 1757.

When compared with their counterparts with D-configuration, the unnatural L-nucleosides mentioned above are endowed with greater antiviral activity (especially against HBV and HIV, for example) and reduced host toxicity in terms of inhibition of cell growth and mitochondrial DNA synthesis. Among these L-nucleosides discussed here, β-L-FD4C was found to be most active against HBV (Lin, et al., *J. Med. Chem.*, 1996, 39, 1757). In fact, β-L-FD4C was about 10-fold more potent against HBV than (–) SddC (3TC), which has been approved recently by the FDA for use in combination therapy against HIV and HBV. The superb antiviral activity observed with β-L-FD4C and β-L-FddC, as well as the clear pharmaceutical potential of other nucleoside analogs, warrant further development of these pharmacological agents as prime candidates for use as anti-viral, including anti-HBV and anti-HIV agents as well as for other uses.

The first synthesis and the antiviral activity assessment of β-L-FD4C was achieved by a group of scientists at Yale University under the supervision of Drs. Lin and Cheng (*J. Med. Chem.*, 1996, 39, 1757). The Yale synthesis consisted of a twelve-step sequence with an overall yield of less than 0.74%. Perhaps the least efficient step in the sequence was the introduction of 5-fluorouracil using a trans-N-glycosylation reaction, which provided only about 10% of the desired β-anomer intermediate. Although this research conducted at Yale represents a major breakthrough in the search of potent antiviral nucleosides with minimal host toxicity, the initial low-yielding synthesis is not amenable for scale-up. Therefore, in order to prepare large amounts of β-L-FD4C for scale-up, clinical testing and ultimately, commercialization, a much more efficient synthesis is desired.

OBJECTS OF THE INVENTION

It is an object of the invention to provide an efficient synthesis of pharmacologically active nucleoside analogs and in particular, 2',3',-dideoxy- (dd) and 2',3'-dideoxy-2', 3'-didehydro- (d4) nucleoside analogs.

It is an additional object of the invention to provide a stereoselective process for the preparation of nucleoside intermediates, and in particular, intermediates which can be used to substantially enhance the stereoselective synthesis of 2',3',-dideoxy- and 2',3'-dideoxy-2',3'-didehydronucleoside analogs.

It is still another object of the invention to provide intermediates in the chemical synthesis of 2',3',-dideoxy- and 2',3'-dideoxy-2',3'-didehydronucleoside analogs which can be used to substantially enhance the stereoselectivity of the introduction of a purine or pyrimidine nucleoside base onto the appropriate position of the intermediate.

These and/or other objects of the invention may be readily gleaned from the description of the invention which follows.

SUMMARY OF THE INVENTION

The present invention relates to methods for substantially enhancing the stereoselective synthesis of β-anomeric nucleoside analogs. In methods according to the present invention, the introduction of a phenylseleno moiety onto a hydroxyl protected lactone sugar precursor (4, below, or its enantiomeric stereoisomer wherein the blocked hydroxyl group is in a β rather than an α orientation) has been obtained in unexpectedly high yields and with unexpectedly high stereospecificity. In certain preferred embodiments, the lactone (ribose precursor) containing a phenylseleno group on the α face (5a, below) is obtained in an amount representing at least about 90% or more of the total amounts of α and β products produced.

In even more preferred embodiments, the amount of α lactone product obtained is at least 95%, even more preferably at least about 97% of the total amount of α and β product produced. The stereospecificity of this reaction is an unexpected result and leads to the

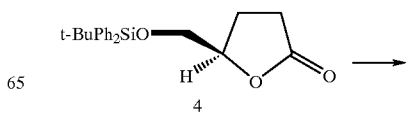

4

-continued

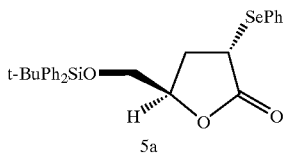

5a synthesis of pharmaceutically active β-L-nucleoside analogs in very high yield.

According to a preferred sequence to synthesize β-L-nucleoside analogs, the phenylseleno containing lactone (5a of FIG. 1 and as set forth above) may be converted to a sugar moiety and used to direct a nucleoside base onto the sugar (generally, a ribose sugar) moiety so that the β-anomer of the nucleoside is produced in a much greater concentration than the α-anomer. This method can be used to synthesize nucleoside analogs and particularly, 2',3',-dideoxy- and 2',3'-dideoxy-2',3'-didehydronucleoside analogs.

The present method addresses and overcomes the difficulties and shortcomings of the prior art and provides processes for producing, in high yield, optically active cis-nucleosides and nucleoside analogs and derivatives of the following formulas (I) and (II):

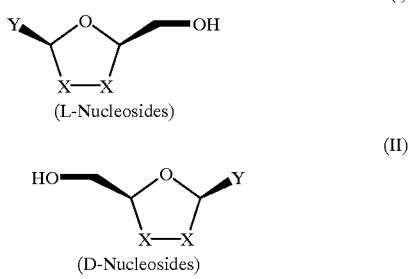

where X is CH or $CH_2$; and
Y is a purine or pyrimidine base or an analog or derivative thereof.

The present invention is directed to a method for enhancing the stereoselective synthesis of either D- or L-β or α-anomeric nucleosides and in particular, introducing a phenylseleno group into a hydroxyl-blocked lactone (4) derived from glutamic acid as set forth in FIG. 1.

The inventive step is accomplished by reacting a phenylseleno-containing compound (e.g., N-phenylseleno-phthalimide or an equivalent bulky seleno-containing compound having the structure ArSeX where Ar is a phenyl or substituted phenyl such as t-butylphenyl or nitro-phenyl and X is a bulky leaving group (such as $^-$OAc, $^-$OC(O)$CF_3$, $^-$SCN, $^-$SO$_2$Ar, $NR_2$, and N-phthalimide) with a hydroxyl protected lactone (4) derived from either D- or L-glutamic acid, which results in the stereoselective synthesis of the desired phenylseleno substituted hydroxyl blocked lactone (5), and ultimately, the desired β-anomeric nucleosides in an unexpectedly high yield. It is noted that the synthesis of L-nucleoside analogs proceeds from D-glutamic acid, whereas the synthesis of D-nucleoside analogs proceeds from L-glutamic acid.

The present invention makes use of the discovery that the introduction of the phenylseleno moiety at the carbon position α to the ketone of the hydroxyl-blocked lactone moiety 4 (above and FIG. 1) using N-phenylseleno-phthalimide is surprisingly highly stereoselective and occurs on the side of the lactone away from interference from the blocked hydroxyl moiety.

In preferred aspects according to the present invention, the present process has the advantage of allowing the preparation of large quantities of a nucleoside of formula (I) (or analogs of derivatives thereof) without using expensive starting materials or taking particularly elaborate steps to separate the anomeric isomers. The processes of this invention produce nucleosides in yields amenable to scale-up and commercial preparation, with high purity and high optical specificity. The processes of the present invention have the further advantage of generating nucleosides whose configuration (as either L- or D-nucleosides) can be easily controlled simply by the selection of the appropriate readily available starting materials (either D-glutamic acid in the case of L-nucleosides or L-glutamic acid in the case of D-nucleosides).

DETAILED DESCRIPTION OF THE INVENTION

Figure 1:
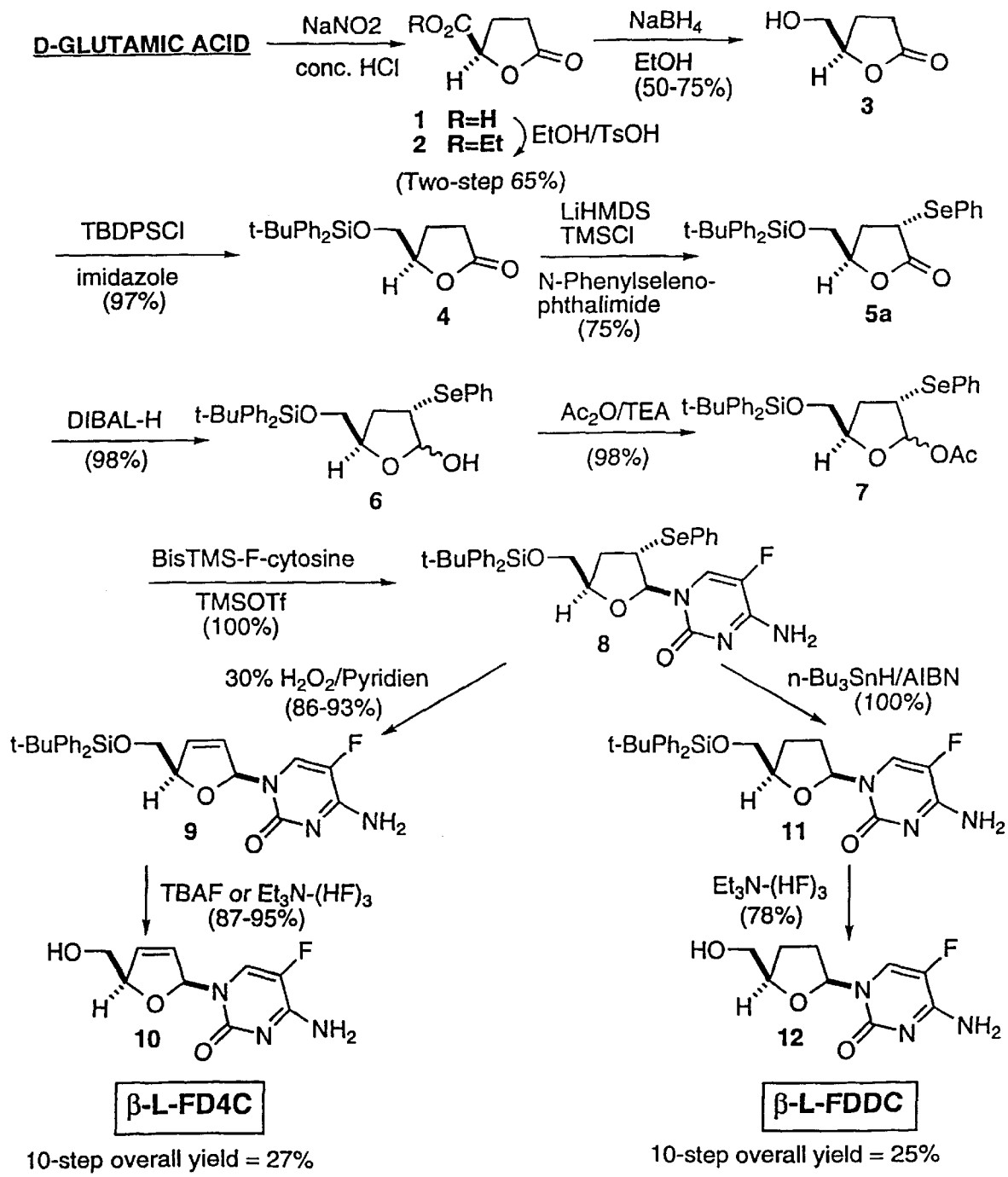
FIG. 1 represents a preferred chemical synthetic scheme for the stereoselective synthesis of β-L-Fd4C and β-L-FddC according to the present invention.

The following definitions will be used throughout the specification to describe the present invention:

The term "nucleoside", "nucleoside analog" or "nucleoside derivative" is used throughout the specification to describe a nucleoside which contains a pyrimidine or purine base attached to a ribose moiety to produce a 2',3'-dideoxynucleoside or a 2',3'-dideoxy-2',3'-didehydronucleoside according to the present invention. The nucleoside analogs according to the present invention may be D-configured ("D") nucleosides or preferably L-configured ("L") nucleosides. The more preferred nucleoside analogs which are produced according to the present invention include β-L-2',3'-dideoxycytidine (β-L-ddC), β-L-5-fluoro-2',3'-dideoxycytidine (β-L-FddC) and β-L-5-fluoro-2',3'-dideoxy-2',3'-didehydrocytidine (β-L-Fd4C). Most preferred is β-L-5-fluoro-2',3'-dideoxy-2',3'-didehydrocytidine (β-L-Fd4C) because of its exceptional anti-HIV and anti-HBV activity.

The terms "L-nucleoside" and "D-nucleoside" are used throughout the specification to describe nucleoside analogs containing a specific chemical configuration of the ribofuranosyl moiety. The L-configuration of the ribose moiety of L-nucleoside compounds of the present invention is an unnatural configuration and contrasts with the natural D-configuration of the ribose moiety found in the naturally occurring nucleosides cytidine, adenosine, thymidine, guanosine and uridine, among others.

The term "pyrimidine" is used to describe heterocyclic compounds of the general class containing such compounds as uracil, thymine and cytosine and their methylated and related analogs (including, pseudouracil, among numerous others). The term pyrimidine includes pyrirndine analogs which mimic such naturally occurring pyrimidine bases in that their structures (the kinds of atoms and their arrangement) are similar to the naturally occuring bases but may either possess additional or lack certain of the functional properties of the naturally occuring bases. Such analogues include those derived by replacement of a CH moiety by a nitrogen atom, (e.g., 5-azapyrimidines such as 5-azacytosine). Included within this term are bases or analogs wherein ring substituents are either incorporated, removed, or modified by conventional substituents known in the art, e.g., halogen, hydroxyl, amino, $C_{1-6}$ alkyl, etc.

Preferred pyrimidine analogs include cytosine analogs which have been substituted at the 5 position, especially with a halogen. Especially preferred is the pyrimidine base 5-fluorocytosine. The pyrimidine bases, analogs and derivatives, which ma y be used in the present invention are generally well known to those skilled in the art.

The term "purine" is used to describe heterocyclic compounds of the general class containing such compounds as hypoxanthine, xanthine, adenine, guanine and their analogs. Such analogs include those derived by replacement of a CH moiety by a nitrogen atom, (e.g. 7-deazapurines, such as 7-deazaadenine or 7-deazaguanine) or both (e.g., 7-deaza, 8-azapurines). By derivatives of such bases or analogs are meant those bases wherein ring substituents are either incorporated, removed, or modified by conventional substituents known in the art, e.g., halogen, hydroxyl, amino, $C_{1-6}$ alkyl, etc.

The term "hydroxyl protected" is used to refer to a hydroxyl group in any one or more of the nucleoside precursors which is protected from undesired reactions, but which may be removed under selective conditions to free the hydroxyl moiety for further reaction, if desired. Hydroxyl protection groups which may be used for this purpose include, for example, trisubstituted silyl groups such as t-butyldimethylsilyl, triphenylsilyl, t-butyldiphenylsilyl as well as trityl, methoxytrityl and pivaloyl groups, among numerous others. The blocking groups may be broadly chosen from the class of silyl blocking groups, ether blocking groups and ester blocking groups, each blocking group being chosen for its ability to sterically hinder introduction of a phenylseleno group on the β face of the hydroxyl protected lactone (4 of FIG. 1) and enhance introduction of the phenylseleno group on the α face of the lactone. Although the above-listed blocking groups are preferred and the t-butyldiphenylsilyl group is especially preferred, any equivalent group which provides a relatively bulky substituent at the hydroxyl-protected position of the lactone ribose precursor 4 (the hydroxyl protected position ultimately becomes the 5' position of the final nucleoside analogs produced) will aid in orienting the introduction of the phenylseleno group in the α position (i.e., on the side of the lactone opposite the hydroxyl protected group).

The term "protected purine" or "protected pyrimidine" is used to describe a purine or pyrimidine in which nitrogen or oxygen groups on the base are protected from undesired reactions. Protecting groups are well known in the art for this purpose and include, for example, trimethylsilyl, dimethylhexylsilyl, t-butyldimethylsilyl, t-butyldiphenylsilyl, triphenylmethyl, alkyl groups and acyl groups, among numerous others.

The term "phenylseleno" is used to describe a phenylseleno-containing group or moiety which is introduced onto a hydroxyl protected lactone (such as compound 4 of FIG. 1 and as otherwise described herein) derived from glutamic acid which will ultimately play an important role in directing the introduction of a nucleoside base onto a sugar (ribose) moiety to produce the final pharmaceutically active β-L- or D-nucleoside analogs. Phenylseleno groups according to the present invention are represented by the formula ArSe, where Ar is a phenyl or substituted phenyl including for example, t-butylphenyl, nitrophenyl, etc. Phenylseleno groups are introduced onto hydroxylprotected lactone (4) utilizing a compound of formula ArSeX, where Ar is a phenyl or substituted phenyl as described above and X is a leaving group which is sufficiently bulky to stereospecifically direct the introduction of the ArSe group onto the α face of hydroxylprotected lactone (4). X is preferably ⁻OAc, ⁻OC(O)CF₃, ⁻SCN, ⁻SO₂Ar, NR₂, or N-phthalimide, most preferably N-phthalimide. Where Ar is a bulky substituent such as a t-butylphenyl group or other bulky phenyl group (other than a phenyl), X may be a halogen such as ⁻Cl, ⁻Br, or ⁻I.

A key feature of the present invention involves the use of a bulky phenylseleno compound, most preferably, N-phenylseleno-phthalimide, to introduce a phenylseleno moiety at the position α to the ketone of a hydroxyl protected lactone (such as compound 4 of FIG. 1) to obtain high stereoselectivity in producing a substituted lactone (5a) in high yield. The production of lactone 5a in such high stereospecific yields (at least about 90%, and in certain instances 97% or greater of the desired stereoisomer 5a) is a surprising result especially considering that the introduction of the phenylseleno group to the lactone 4 using phenylseleno bromide or phenylseleno chloride has considerably less stereoselective control. In the present invention, quite unexpectedly, the use of N-phenylseleno-phthalimide (or an equivalent phenylseleno compound) to introduce the phenylseleno group provides the desired stereoisomer exclusively in about 75% yield, greatly improving the poor selectivity (α/β=2.5:1) and yield (10%) previously reported in the art (Chu, et al., *J. Org. Chem.*, 1990, 55, 1418.

Another feature of the processes of the present invention is the optimization of the reaction conditions for the steps following the addition of the phenylseleno group to ensure high yield (>90%) for each step.

In a preferred process according to the present invention to produce L-nucleosides, pure D-glutamic acid is converted in a stepwise fashion to a hydroxyl protected lactone of formula 4 of FIG. 1, which is then reacted with N-phenylseleno-phthalimide to exclusively obtain the lactone of formula 5a. The lactone is subsequently reduced to produce the diastereomeric sugar mixture 6, which is subsequently acetylated and condensed with silylated 5-fluorocytosine to produce 2'-phenylseleno-substituted nucleoside analog (compound 8 of FIG. 1) which may be treated with a reducing agent to produce hydroxyl protected 2',3'-dideoxynucleoside (dd) analog 11 or alternatively, analog 8 may be treated with a mixture of hydrogen peroxide in pyridine or a related oxidizing agent to produce the hydroxyl protected 2',3'-dideoxy-2',3'-didehydro nucleoside (d4) analog 9. The hydroxyl protected nucleoside analogs 9 and 11 are deprotected using methods well known in the art to product the corresponding β-L-5-Fluoro-2',3'-dideoxycytidine (β-L-FddC) and β-L-5-fluoro-2',3'-dideoxy-2',3'-didehydrocytidine (β-L-Fd4C).

As previously indicated, the primary aspect of the present invention is the stereoselective introduction of the phenylseleno group at the carbon α to the ketone of hydroxyl protected lactone 4 to produce hydroxyl protected lactone 5a. Lactone 4 may be provided by any synthetic method available in the art, but preferably proceeds according to the synthetic scheme set forth in FIG. 1 starting from glutamic acid. It is noted that the synthetic scheme set forth in FIG. 1 is directed to the synthesis of L-nucleosides, starting from D-glutamic acid. If the synthetic target compound is a D-nucleoside, the starting material following the general synthetic scheme described in FIG. 1 is L-glutamic acid. Preferably, but not necessarily, the synthetic steps to produce the final D-nucleoside analogs may be identical to the steps set forth in FIG. 1.

Lactone 5a or the corresponding enantiomeric lactone derived from L-glutamic acid (which is used to produce D-nucleosides), are intermediates useful to efficiently synthesize pharmacologically active L- and D-2',3'-dideoxy- (dd) and 2',3'-dideoxy-2',3'-didehydro- (d4) nucleosides according to the present invention.

Lactone 4, the synthetic precursor to phenylseleno-substituted lactone 5, may be synthesized by any synthetic method available in the art, but is preferably synthesized from enantiomerically pure D- or L- glutamic acid as the starting material. In a preferred method as set forth in FIG. 1, in order to synthesize lactone 4, D-glutamic acid is reacted in the presence of acid to produce lactone acid 1, which is subsequently esterified in an appropriate alcohol and acid, to produce lactone ester, 2. The ester moiety is thereafter reduced using any common hydride reducing agent, such as one or more of the various borohydrides (including sodium, lithium, tetrabutyl ammono borohydride) or various aluminum hydrides (including Met-AlH$_4$, Met-AlH(OR)$_3$, etc.) to produce lactone alcohol 3. Lactone alcohol 3 is then reacted with a compound which provides a bulky protecting group R on the alcohol, for example, t-butyldiphenylsilyl chloride, which serves to protect the free hydroxyl group of lactone 3 from reacting in subsequent synthetic steps. Protecting group R may be a bulky silyl group such as triethylsilyl, t-butyldimethylsilyl, t-butyldiphenylsilyl (pictured in compound 4 in FIG. 1), among others, a bulky ester group such as a pivaloyl [Me$_3$CC(O)$^-$] group, among others and bulky ether groups such as triphenylmethyl ether (trityl) or p-methoxyphenyl-diphenylmethyl ether (methoxytriyl). These bulky hydroxy blocking groups, in combination with the bulky phenylseleno compounds produce highly stereoselective introduction of the phenylseleno moiety onto the a face at the carbon a to the lactone moiety of hydroxyl protected lactone 4.

In producing the phenylselenated hydroxyl protected lactone 5a, lactone 4 is first reacted with a strong base such as lithium bis(trimethylsilyl) amide followed by reaction with a silylprotecting group such as trimethylsilylchloride, among others. Sodium or potassium bis(trimethylsilyl) amide may be used as the base in this reaction as well as other equivalent bases strong enough to abstract a proton from the carbon α to the ketone moiety of lactone 4 as well as other strong bases such as butyl lithium (BuLi), lithium diethylamide (LDA), among other strong bases. The enol intermediate formed is then stabilized with a trimethylsilyl group. After silylation, the trimethylsilylated enol intermediate is then reacted with N-phenylseleno-phthalimide to introduce the phenylseleno group at the carbon position a to the carbonyl. As one of ordinary skill in the art will readily recognize, other methods for introducing the phenylseleno group onto the carbon α to the carbonyl of the lactone moiety using N-phenylseleno-phthalimide or an equivalent phenylseleno-containing compound may also be used, but these are generally less efficient than the method which has been outlined in detail above.

The phenylseleno substituted lactone 5a is thereafter converted to the appropriate dideoxy- or dideoxy-didehydro nucleoside analog. This is generally done by converting (usually, by reducing) the carbonyl moiety of the lactone to a reactive intermediate which can condense with a purine or pyrimidine base in a glycosylation reaction. This may be accomplished in a number of ways, but a preferred method involves the conversion of the hemi-acetal hydroxyl group of a ribose sugar (such as compound 6 of FIG. 1) to an acetate group (compound 7) and then condensing a purine or pyrimidine base onto the acetylated C-1 carbon of the ribose sugar. Pursuant to a preferred method, as depicted in the synthetic scheme set forth in FIG. 1, phenylselenated lactone 5a is reduced to hemi-acetal 6, by reducing the carbonyl to a secondary alcohol using DIBAL-H. Any number of other reducing agents such as the borohydride reagents or aluminum hydride reagents, among others, may be used to reduce the carbonyl to the alcohol, but DIBAL-H is preferred, because the reaction with this reagent is nearly quantitative (98% yield). Hemi-acetal 6 is then converted to C-1 acetylated ribose 7. In the preferred synthetic scheme, the acetylation reaction is conducted in an acetic anhydride/triethylamine mixture, although any number of acetylating reagents may be used, generally in the presence of an acid scavenger such as an amine.

Acetylated ribose 7 is used in a condensation reaction to condense a pyrimidine or purine base onto the acetylated ribose. In the preferred method set forth in FIG. 1, a bis-trimethylsilylated 5-Fluorocytosine base is condensed onto acetylated (or other esterified compound such as a benzoylated compound, etc.) ribose 7 in quantitative yield in the presence of a Lewis acid such as trimethylesilyltriflate (TMSOTf), SnCl$_4$, TiCl$_2$(OR)$_2$ TiCl(OR)$_3$ or TiCl$_4$, among numerous other Lewis Acids well known in the art. Preferably this condensation reaction is performed in the presence of trimethylsilyl triflate (TMSOTf), to produce the 2'-α-phenylseleno substituted nucleoside analog 8. To prepare the 2',3'-dideoxynucleoside analog 12, nucleoside analog 8 is reduced preferably with a hydride reducing agent, preferably tri-n-butyltin hydride (n-Bu$_3$SnH) in the presence of AlBN$_3$ or Et B/O$_2$, followed by removal of the 5'-OH blocking group to produce the preferred compound β-L-5-fluoro-2', 3'-dideoxycytidine (β-L-FddC). Alternatively, nucleoside analog 8 may be reacted with an appropriate oxidizing agent (for example, a peroxide such as hydrogen peroxide in pyridine, or meta-chloroperbenzoic acid, among numerous other peroxides) to produce the 2',3'-dideoxy-2',3'-didehydro nucleoside analog 10, which is treated to remove the hydroxyl protecting group to provide β-L-5-fluoro-2',3'-dideoxy-2',3'-didehydrocytidine (β-L-FD4C).

While the preferred synthetic chemical method has been described above, one of ordinary skill in the art will recognize that substitute or equivalent steps may be used to obtain the same results. For example, one of ordinary skill may readily substitute for certain of the reagents and virtually all of the solvents used to produce an intermediate as set forth in FIG. 1. Formation of lactone 1 and lactone ester 2, for example, may be readily formed using any appropriate lactone-forming reagent or reagent combination and any appropriate alcohol, including methanol and propanol, may be used to provide an ester. The hydrogenating agent sodium borohydride may be replaced by virtually any other compatible borohydrate or aluminum hydride and any appropriate solvent instead of ethanol may be used. Any bulky hydroxyl protecting group may be used to prevent further reaction of the alcohol group and help to orient the introduction of the phenylseleno group.

Stereospecific introduction of the phenylseleno group at the carbon α to the carbonyl in lactone 4 may be accomplished using a number of strong bases other than lithium (bis)trimethylsilyl) amide, for example BuLi and LDA. The reaction proceeeds through enol formation and a silyl blocking group such as trimethylsilyl, among others such as t-butyldimethylsilyl and other equivalent silyl protecting groups, may be used to stabilize the enol structure to which the phenylselenogroup will be added. In choosing a silyl protecting group for this purpose, one of ordinary skill will understand that the choice of silyl protecting will be made based upon the ability of the silyl group to stabilize the enol intermediate as well as its relative ease of removal. Phenylseleno phthalimide is the preferred phenylselenating agent used in the present invention, but any phenylselenating agent which contains a bulky leaving group equivalent to the phthalimide group as described hereinabove may be used. One of ordinary skill may readily modify the phenyl substituents in conformity with a change in the bulkiness of the leaving group (ArSeX) in order to influence the stereoselectivity of the phenylseleno introduction).

The following presentation of the synthesis of β-L-FddC (β-L-5-Fluoro-2',3'-dideoxycytidine and β-L-FD4C (β-L-5-fluoro-2',3'-dideoxy-2',3'-didehydrocytidine) illustrates the present invention in a manner of which it can be practiced but, as such, should not be construed as limiting the overall scope of the processes of this invention, especially in relation to obvious variants, substitutions and equivalents.

EXAMPLES

Example 1

The preferred embodiment of this invention is outlined in FIG. 1 and detailed below. References to the numbered compounds are the same as those found in the synthetic scheme presented in FIG. 1. In this embodiment, the synthesis of the target compound 12 β-L-5-fluoro-2',3'-dideoxycytidine (β-L-FddC) and 10 β-L-5-fluoro-2',3'-dideoxy-2',3'-didehydrocytidine (β-L-FD4C) is completed in ten-steps with an overall yield of 25% and 27%, respectively. The least efficient step in this sequence is 75% (from 4 to 5a). The average yield for each step is approximately 88%, making this synthetic scheme commercially viable.

Materials and Methods

All reagents were purchased commercially except where indicated as otherwise. Solvents were distilled prior to use. Melting points were determined using a MelTemp apparatus and are uncorrected. Proton NMR spectra were recorded on a Varian EM390 or Bruker WM 250 instrument and reported as ppm (delta) downfield from $(CH3)_4Si$. Ultraviolet spectra were recorded on a Beckman 25 spectrophotometer. Analytical thin-layer chromatography (TLC) was performed using Merck EM Silica Gel 60 precoated sheets. Column chromatography employed Merck EM silica gel using standard organic solvents Detailed reaction conditions and characterizations of each intermediate (including $^1$H NMR, $^{13}$C NMR and LRMS or HRMS and elemental analysis data for compounds 8 to 12) are provided in this section.

Procedure

Preparation of Lactone Ester 2

To a suspension of D-glutamic acid (50.0 g) in water (70 mL) was added conc. HCl (70 mL) at 0° C., followed by slow addition of a solution of $NaNO_2$ (35.0 g) in water (75 mL) over a period of 2 hr. The reaction was then allowed to warm to r.t. and stirred for additional 15 hr. The solvent was evaporated in vacuo (below 50° C.) to dryness. The reaction mixture was then stirred with EtOAc (150 mL). The insoluble fraction was filtered off and the solids were washed with EtOAc (2×50 mL). The combined filtrates were dried ($Na_2SO_4$). The solvent was evaporated in vacuo to afford 45 g (~100%) of thecrude lactone (1) as a pale yellow syrup.

A solution of the above crude acid and the catalytic amount of p-TsOH (1.0 g) in EtOH (65 mL) and benzene (150 mL) was refluxed for 5 hr, and the solvent was distilled off under atmospheric pressure until the b.p. raised to 79° C. The reaction mixture was cooled to r.t., and then diluted with benzene (500 mL). The resulting reaction mixture was washed with water, 10% $Na_2CO_3$ solution, water and then dried with $Na_2SO_4$. The solvent was evaporated and the residue was distilled under high vacuum to provide 35.0 g (65% two-step yield) of the desired ester-lactone (2).

Analysis of Lactone Ester 2

$^1$H NMR of 2 ($CDCl_3$, 300 MHz): δ4.87 (m, 1H), 4.14 (q, 2H), 2.55–2.23 (m, 4H), 1.22 (t, 3H).

Preparation of Lactone Alcohol 3

To an ethanol solution (48 mL) of $NaBH_4$ (2.90 g) was added at 0° C. an ethanol solution (72 mL) of the ester-lactone 2 (17.3 g, 109.5 mmol) over 10 min. The resulting reaction mixture was stirred at room temperature for 1 hr. The reaction was then quenched at 0° C. with 10% HCl until the pH of the soluton was 3. The solids were filtered off. The filtrates were conc. in vacuo, and the resulting residue was coevaporated with MeOH three times. The resulting residue was then purified with silica gel chromatography (10–20% $EtOH/CH_2Cl_2$) to afford 9.5 g (75%) of the desired alcohol 3 as a colorless liquid.

Analytic Data for Lactone Alcohol 3

$^1$H NMR of 3 ($CDCl_3$, 300 MHz): δ4.72 (m, 1H), 3.99 (dd, J=3.1 Hz, J'=12.7 Hz, 1H), 3.72 (dd, J=4.8 Hz, J'=12.6 Hz, 1H), 2.76–2.18 (m, 4H).

Procedure for Silylether Lactone 4

To a dichloromethane solution (62 mL) of 3 (5.10 g, 43.97 mmol) was added imidazole (3.89 g, 57.16 mmol) and t-butylchlorodiphenylsilane (13.30 g, 12.58 mL) at 0° C. The reaction was stirred at 0° C. for 1 hr and then at r.t. for 2 hr. The reaction mixture was diluted with $CH_2Cl_2$ (150 mL), and washed with water (3×40 mL) and brine (40 mL). The organic layer was dried and conc. in vacuo to yield a residue, which was chromatographed (20–30% EtOAc/Hexanes) to afford 15.2 g (97%) of the desired silylether 4 as a pale yellow syrup.

Analytical Data for Silylether Lactone 4

$^1$H NMR of 4 ($CDCl_3$, 300 MHz): δ7.70–7.39 (m, 10H), 4.61 (m, 1H), 3.90 (d, J=3.3 Hz, J'=11.4 Hz, 1H), 3.70 (dd, J=3.3 Hz, J'=11.4 Hz, 1H), 2.70 (m, 1H), 2.53 (m, 1H), 2.26 (m, 2H), 1.08 (s, 9H).

Preparation of Phenylselenide Lactone 5a

Lithium bis(trimethysilyl) amide in THF (1M, 32.2 mL, 32.20 mmol) was added to 6 ml of THF under $N_2$, and cooled to –78° C. Silylether lactone 4 (10.36 g, 29.30 mmol) dissolved in 20 ml THF was added slowly to the above solution in 45 min at –78° C. One hour after the addition, TMSCl (5.0 mL, 64.46 mmol) was added dropwise over 5 min. This mixture was then stirred at –78° C. for 1 hr, and then warmed to room temperature and stirred for 2 hr. The reaction mixture was then cooled to –78° C., and N-phenylseleno-phthalimide (11.0 g, 36.40 mmol) was added through a powder addition funnel over 1 hr. Stirring at –78° C. was continued for 3 h, followed by warming to room temperature for 30 min. The reaction mixture was poured into 150 ml of $NaHCO_3$ solution and 300 mL ether, and then extracted twice with $NaHCO_3$ and once with NaCl solution. The aqueous layers were re-extracted with 100 mL of ether, and the organic layers were combined, dried over $MgSO_4$, filtered, and the solvent was removed in vacuo. Purification of the crude material by column chromatography afforded 11.20 g of the trans-isomer (yield 75%). A minor quantity of the cis-isomer 200 mg (1%) was also obtained.

Analytical Data for Phenylselenide Lactone 5a $^1$H NMR of 5a ($CDCl_3$, 300 MHz): δ7.75–7.32 (m, 15H), 4.40 (m, 1H), 4.16 (dd, J=5.4 Hz, J'=9.2 Hz, 1H), 3.90 (dd, J=2.9 Hz, J'=11.5 Hz, 1H), 3.66 (dd, J=3.1 Hz, J'=11.5 Hz, 1H), 2.75 (m, 1H), 2.33 (m, 1H), 1.10 (s, 9H).

$^{13}$C NMR of 5a ($CDCl_3$, 75 MHz): δ176.1, 135.8, 135.7, 135.6, 132.9, 132.5, 130.1, 129.5, 129.1, 128.0, 127.2, 78.8, 65.0, 37.3, 32.5, 27.0, 19.3.

Preparation of Lactol 6

A toluene solution (10 mL) of the Phenylselenide lactone 5a (1.63 g, 3.20 mmol) was treated at −78° C. with DIBAL-H (2.35 mL, 1.5 M). After 1 hr, an additional amount of DIBAL-H (0.32 mL) was added. After 30 min, the reaction was quenched at −78° C. with a saturated solution of sodium potassium tartrate (40 mL). The reaction mixture was warmed to r.t. and extracted with EtOAc (2–50 mL). The combined organic layers was further washed with sodium potassium tartrate saturated solution until a clear solution was obtained. The organic layer thus obtained was dried and evaporated in vacuo. The residue was chromatographed (10–20% EtOAc/Hexanes) to provide 1.60 g (98%) of the desired lactol 6.

Analytical Data for Lactol 6

$^1$H NM of 6 (CDCl$_3$, 300 MHz): δ7.80–7.26 (m, 15H), 5.64–5.44 (m, 1H), 4.45 (m, 1H), 4.10–3.52 (m, 4H), 2.79–2.00 (m, 2H), 1.13–1.06 (m, 9H).

Preparation of 1' Sugar Acetate 7

To a dichloromethane solution (18 mL) of the lactol 6 (4.50 g, 8.80 mmol) was added triethylamine (1.59 mL, 11.44 mmol) and acetic anhydride (1.08 mL, 11.44 mmol) at 0° C. A catalytic amount of DMAP was also added. The reaction was stirred at 0° C. for 1 hr and then at r.t. for 12 hr. The reaction was quenched with a NaHCO$_3$ saturated solution (20 mL), and the resulting reaction mixture was extracted with CH$_2$Cl$_2$ (2×100 mL). The combined organic layers were washed with brine, and dried and conc. in vacuo. The residue was purified through a short pack of silica gel column (using 15% ethyl acetate/hexanes as eluant) to provide 4.75 g (98%) of the corresponding 1'-Sugar acetate derivative 7 as a thick oil.

Analytical Data for 1'-Sugar Acetate $^1$H NMR (300 MHz, CDCl$_3$): δ7.74–7.20 (m, 15H), 6.44–6.22 (m, 1H), 4.44–3.52 (m, 4H), 2.58–2.08 (m, 2H), 1.86 & 1.55 (s, 1H), 1.02 & 0.92 (s, 9H). FAB mass calc. for C$_{29}$H$_{35}$O$_4$SiSe (MH+): 554, found: 554.

Preparation of Phenylselenide Nucleoside 8

A mixture of 5-Fluorocytosine (1.11 g, 8.58 mmol) and ammonium sulfate (40 mg) in (TMS)$_2$NH was heated to reflux for 2 hr. A clear solution was resulted. The reaction mixture was cooled to r.t., and the solvent was removed in vacuo. The resulting white solids (bis-TMS-5-FC) were dried under high vacuum for 30 min.

To the bis-TMS-5-FC thus prepared was added a dichloroethane solution (30 mL) of 1' sugar acetate derivative 7 (4.75 g, 8.58 mmol). To the above solution was then added at 0° C. a dichloroethane solution (10 mL) of TMSOTf (1.99 mL, 10.30 mmol). The reaction mixture was stirred at 0° C. for 30 min, and then at room temperature for 90 min. At this point, the reaction was quenched with NH$_4$Cl saturated solution (30 mL), and extracted with dichloroethane (250 mL). The organic layer was washed with brine, dried and conc. in vacuo. The resulting residue was chromatographed (60–80% EtOAc/Hexanes, then 10% EtOH/CH$_2$Cl$_2$) to afford 5.40 g (100%) of the desired product as white foam.

Analytic Data for Phenylselenide Nucleoside 8

$^1$H NMR of 8 (300 MHz, CDCl$_3$): δ8.00 (d, J=5.5 Hz, 1H), 7.66–7.25 (m, 15H), 6.13 (dd, J=1.4 Hz, J'=4.9 Hz, 1H),4.32(m, 1H~), 4.11 (d, J=11.2 Hz, 1H), 3.85 (dd, J=6.5 Hz, J'=11.6 Hz, 1H), 3.69 (dd, J=2.3 Hz, J'=11.8 Hz, 1H), 2.47 (m, 1H), 2.06 (m, 1H), 1.11 (s, 9H).

$^{13}$C NMR of 8 (CDCl$_3$, 75 MHz): δ156.2, 156.0, 151.9, 137.8, 135.8, 135.7, 135.5, 134.6, 132.6, 132.3, 130.2, 130.0, 129.4, 128.6, 128.1, 127.9, 126.9, 126.1, 125.7, 91.3, 80.5, 65.1, 44.9, 32.3, 27.1, 19.3.

FAB mass calc. for C$_{31}$H$_{35}$FN$_3$O$_3$SiSe (MH$^+$): 624, found: 624.

Preparation of Silylether Didehydro Nucleoside 9

To a THF solution of phenylselenide 8 (437 mg, 0.702 mmol) was added at 0° C. 30% wt. hydrogen peroxide aqueous solution (0.22 mL, 7.02 mmol). The reaction was stirred at 0° C. for 1 hr. At this point, pyridine (0.57 mL, 7.02 mmol) was added at 0° C. The reaction was stirred at r.t. for 3 hr. The reaction mixture was then diluted with EtOAc (50 mL) and Et$_2$O (10 mL), and then washed with NaHCO$_3$ saturated solution and brine. The organic layer was dried over Na$_2$SO$_4$, and then evaporated in vacuo to afford a residue, which was purified with silica gel chromatography (5–10% EtOH/CH$_2$Cl$_2$) to provide 280 mg (86%) of the desired Silylether didehydro nucleoside 9.

Analytical data for Silylether Didehydro Nucleoside 9

$^1$H NMR of 9 (CDCl$_3$, 300 MHz): δ8.95 (bs, 1H), 7.74–7.34 (m, 10H), 6.98 (d, J=1.5Hz, 1H), 6.10 (d, J=5.9 Hz, 1H), 5.92 (d, =5.7 Hz, 1H), 5.83 (bs, 1H), 4.85 (s, 1H), 3.95 (dd, J=3.1 Hz, J'=11.6 Hz, 1H), 3.77 (dd, J=3.4 Hz, J'=11.7 Hz, 1H), 1.05 (s, 9H).

$^{13}$C NMR of 9 (CDCl$_3$, 75 MHz): δ158.6, 158.4, 154.4, 138.4, 135.7, 135.2, 133.1, 132.9, 132.7, 130.1, 130.0, 127.9, 127.7, 125.4, 125.0, 91.2, 87.2, 65.3, 27.0, 19.3.

FAB mass calc. for C$_{25}$H$_{29}$FN$_3$O$_3$Si (MH$^+$): 467, found: 467

Preparation of Silylether Didedeoxy Nucleoside 10

Preparation (a) A THF solution (26 mL) of 5'-silylether 9 (0.71 g, 1.53 mmol) was treated at 0° C. with tetrabutylammonium fluoride (TBAF) (3.81 mL, 1M, 3.81 mmol). The reaction was stirred at 0° C. for 30 min, and then at r.t. for 2 hr. At this point, the solvent was removed in vacuo. The resulting residue was purified by silica gel chromatography (80% EtOAc/Hexanes to 10–20% EtOH/CH$_2$Cl$_2$) to provide 331 mg (95%) of the desired product β-L-5-fluoro-2',3'-dideoxy-2',3'-didehydrocytidine (β-L-FD4C) 10 as white foam.

Preparation (b) To a 0° C. cooled THF solution of silylether 9 (321 mg, 0.690 mmol) was added triethylamine-trihydrofluoride (0.449 mL, 2.72 mmol). After stirring at r.t. for 5 hr, second dose of reagent was added at 0° C. The reaction mixture was stirred at r.t. for 15 hr. The solvent was then removed in vacuo. The residue was chromatographed (5–10–20% EtOH/CH$_2$Cl$_2$) to afford 146 mg (94%) of the desired product β-L-5-fluoro-2',3'-dideoxy-2',3'-didehydrocytidine (β-L-FD4C) 10.

Analytical data for δ-L-5-fluoro-2',3'-dideoxy-2',3'-didehydrocytidine (β-L-FD4C) 10

$^1$H NMR of 10 (DMSO-d6, 300 MHz): δ8.01 (d, J=7.2 Hz, 1H), 7.77 (bs, 1H), 7.52 (bs, 1H), 6.81 (d, J=1.1 Hz, 1H), 6.30 (dd, J=1.2 Hz, J'=5.9 Hz, 1H), 5.86 (dd, J=1.3 Hz, J'=5.9 Hz, 1H), 5.07 (bs, 1H), 4.76 (s, 1H), 3.31–3.60 (m, 2H).

FAB mass calc. for C$_9$H$_{11}$FN$_3$O$_3$ (MH$^+$): 228, found: 228.

Preparation of Silylether Didedeoxy Nucleoside 11

To a degassed benzene solution (5 mL) of 8 (323 mg, 0.519 mmol) and catalytic amount of AIBN was added tributyltin hydride (0.279 mL, 1.038 mmol). The reaction mixture was heated to reflux for 1.5 hr. The reaction mixture was then cooled to room temperature, the solvent was removed in vacuo. The residue was purified by silica gel chromatography (5–10% EtOH/CH$_2$Cl$_2$) to afford 240 mg (100%) of the desired Silylether Didedeoxy Nucleoside 11.

Analytical data for Silylether Didedeoxy Nucleoside 11

$^1$H NMR of 11 (CDCl$_3$, 300 Mhz): δ8.17 (d, J=4.2 Hz, 1H), 7.71–7.28 (m, 10H), 6.40 (bs, 1H), 5.98 (d, J=6.0 Hz, 1H), 4.16–4.09 (m, 2H), 3.75–3.70 (m, 1H), 2.60–1.78 (m, 4H).

FAB mass calc. for C$_9$H$_{13}$FN$_3$O$_3$ (MH$^+$): 230, found: 230.

Preparation of β-L-5-fluoro-2',3'-dideoxycytidine (β-L-FddC) 12

To a THF solution (10 mL) of 11 (240 mg, 0.52 mmol) was added at 0° C. of Et₃N-(HF)₃ (0.339 mL, 2.08 mmol). The reaction mixture was stirred at r.t. for 3 hr. At this point, additional six equivalents of the same desilylating agent was added and the reaction mixture was stirred overnight at r.t. The solvent was then removed in vacuo, and the resulting residue was chromatographed (10–20% EtOH/CH₂Cl₂) to provide 95 mg (78%) of the desired β-L-FddC 12 as white foam.

Analytical data for δ-L-5-fluoro-2',3'-dideoxycytidine 12 (β-L-FddC)

¹H NMR of β-L-FddC (DMSO-d6, 300Mhz): δ8.26 (d, J=7.4 Hz, 1H), 7.65 (bs, 1H), 7.43 (bs, 1H), 5.83 (m, 1H), 5.15 (bs, 1H), 4.01 (m, 1H), 3.72 (d, J=11.7 Hz, 1H), 3.52 (d, J=11.9 Hz, 1H), 2.27–2.20 (m, 1H), 1.91–1.75 (m, 3H).

Example 2

Prior Art Synthesis of PhenylSelenide Lactone (5a)

The following synthesis of Phenylselenide lactone (5a) from Silylether lactone (4) followed the teachings of the prior art. Chu, et al. *J. Org. Chem.*, 55, 1418 (1990) and Ryl, et al., *Synthesis* 874 (1977). Essentially, the art utilized phenylselenium bromide to introduce a phenylseleno group onto an enol ether. The stereoselectivity of the introduction of the phenylseleno group was significantly less specific than for the method according to the present invention.

A THF solution (106 ml) of lactone 4 (12.50 g, 35.27 mmol) was treated at −78° C. with LiHMDS (35.30 ml, 1M) for 15 minutes; neat TMSCl (4.48 ml, 35.27 mmol) was then added over a 2 minute period. The resulting reaction mixture was then stirred at −78° C. for 30 minutes and then at room temperature for 2 hours. The reaction was then quenched with NH₄Cl saturated solution. The reaction solvent was partially removed in vacuo. The resulting reaction mixture was extracted with EtOAc (3×100 ml). The combined organic layers were washed with brine and dried Na₂SO₄. Upon evaporation, the resulting rtesidue was purified with silica gel chromatography (10–20% EtOac/Hexanes) to afford 10.80 g (60%) of the desired 2'-phenylselenide 5a alone with 4.40 g (24%) of its isomer 5b.

A THF solution (35 ml) of 2'-p-phenylselenide derivative 5b (4.40 g, 8.64 mmol) was treated with DBU (3.10 ml, 20.74 mmol) at room temperature for 24 hours. The solvent was then partially removed in vacuo. The reaction mixture was diluted with EtOac (150 ml), and washed with NaHCO₃ saturated solution and brine. The organic layer was dried, evaporated and purified to provide 2.3 g (52%) of the 2'-α-phenylselenide 5a along with 1.3g (30%) of the recovered S.M. (5b).

Analytic Data

¹H NMR of 5a (CDCl₃, 300 MHz): δ7.75–7.32 (m, 15H), 4.40 (m, 1H), 4.16 (dd, J=5.4 Hz, J'=9.2 Hz, 1H), 3.90 (dd, J=2.9 Hz, J'=11.5 Hz, 1H), 3.66 (dd, J=3.1Hz, J'=11.5 Hz, 1H), 2.75 (m, 1H), 2.33 (m, 1H), 1.10 (s, 9H).

¹³C NMR of 5a (CDCl₃, 75 MHz): δ176.1, 135.8, 135.7, 135.6, 132.9, 132.5, 130.1, 129.5, 129.1, 128.0, 127.2, 78.8, 65.0, 37.3, 32.5, 27.0, 19.3.

¹H NMR of 5b (CDCl₃, 300 MHz): δ7.70–7.26 (m, 15H), 4.54 (m, 1H), 4.07 (dd, J=9.5 Hz, 1H), 3.76–3.63 (m, 2H), 2.68 (m, 1H), 2.27 (m, 1H), 1.10 (s,9H). ¹³C NMR of 5b (CDCl₃, 75 MHz): δ175.8, 135.7, 135.5, 133.0, 132.9, 130.0, 129.4, 128.9, 127.9, 127.5, 78.8, 64.8, 37.1, 31.8, 26.9, 19.4.

It is to be understood that the examples and embodiments described hereinabove are for the purposes of providing a description of the present invention by way of example and are not to be viewed as limiting the present invention in any way. Various modifications or changes that may be made to that described hereinabove by those of ordinary skill in the art are also contemplated by the present invention and are to be included within the spirit and purview of this application and the following claims.

We claim:

1. A diastereoselective process for producing a lactone of formula (5a) in a mixture of lactones of formula 5(a) and 5(b)

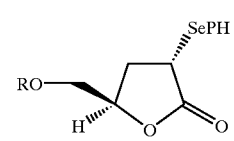

(5a)

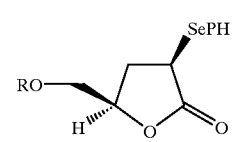

(5b)

comprising the steps of:

1) reacting a hydroxyl protected lactone of formula (4) where R is a hydroxyl

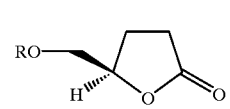

(4)

protecting group (A) selected from the group consisting of t-butyldiphenylsilyl, triphenylsilyl, t-butyldimethylsilyl, trityl, methoxytrityl and pivaloyl with an effective amount of a strong base followed by introduction of a silyl blocking group (B) in a second step to produce a silyl-protected enol ether;

2) reacting the silyl-protected enol ether product obtained from step 1 with a phenyl-seleno compound of formula ArSeX where Ar is phenyl or a substituted phenyl and X is selected from the group consisting of ⁻OAc, ⁻OC(O)CF₃, ⁻SCN, ⁻SO₂Ar, NR₂, and N-phthalimide, to produce the compound of formula 5a, said compound of formula 5a being produced in a proportion of at least about 90% by weight of said mixture of the compounds of formula 5a and 5b without further reaction.

2. The process according to claim 1 wherein said base is selected from the group consisting of butyl lithium, lithium diethylamide, lithium (bis)trimethylsilylamide, sodium (bis) trimethylsilylamide and potassium (bis)trimethylsilylamide.

3. The process according to claim 1 wherein said silyl blocking group (B) is a trimethylsilyl group.

4. A diastereoselective process for producing L-nucleosides of formula

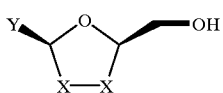

(I)

wherein R is a purine or pyrimidine base and X is CH or CH$_2$, comprising:

1) synthesizing a compound of formula (5a) in a mixture of compounds of formulas (5a) and (5b)

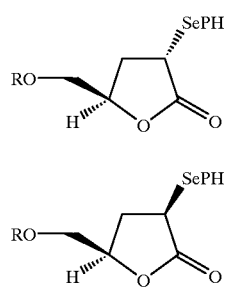

5a

5b where R is a bulky hydroxyl protecting group selected from the group consisting of t-butyldiphenylsilyl, triphenylsilyl, t-butyldimethylsilyltrity, methoxytrityl and pivaloyl, from a compound of formula (4)

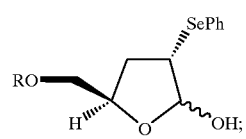

4 by reacting said compound (4) with an effective amount of a strong base in a first step followed by introduction of a silyl blocking group in a second step to produce a silyl-protected enol ether, followed by reacting said silyl protected enol ether with a phenylseleno-containing compound of formula ArSeX where Ar is phenyl or phenyl-substituted and X is selected from the group consisting of $^-$OAc, $^-$OC(O)CF$_3$, $^-$SCN, $-$SO$_2$Ar, NR$_2$, and N-phthalimide to produce a mixture of the phenylselenated lactone compounds of formulas (5a) and (5b), said compound of formula (5a) consisting of at least about 90% by weight of said mixture;

2) reducing the lactone moiety of compound (5a) to produce hemi-acetal (6):

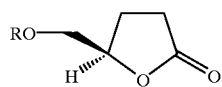

(6)

3) esterifying hemi-acetal (6) to produce esterified compound of formula (7), where E is an ester group;

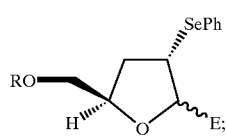

(7)

4) condensing a purine or pyrimidine base onto said esterified compound (7) to produce a nucleoside of formula (8):

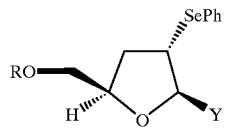

(8)

where Y is a purine or pyrimidine base.

5. The method according to claim 4 wherein said formula (8) nucleoside is further subjected to oxidizing conditions followed by hydroxyl deprotection to produce a 2',3'-dideoxy-2',3'-didehydro nucleoside of formula (10):

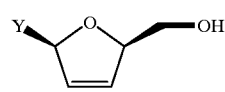

(10)

6. The process according to claim 4, wherein Y is a pyrimidine base.

7. The process according to claim 5, wherein said pyrimidine base is cytosine.

8. The process according to claim 5, wherein said pyrimidine base is 5-fluorocytosine.

9. The process according to claim 4, further comprising the step of reducing the nucleoside of formula (8) to produce a 2',3'-dideoxynucleoside derivative of formula 12.

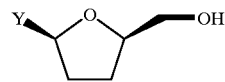

(12)

10. The process according to claim 9, wherein Y is a pyrimidine base.

11. The process according to claim 10, wherein the pyrimidine base is cytosine.

12. The process according to claim 10, wherein the pyrimidine base is 5-flourocytosine.

13. The process according to claim 9 wherein X is N-phthalimide.

14. The process according to claim 9 wherein said strong base is selected from the group consisting of butyl lithium, lithium diethylamide, lithium (bis)trimethylsilylamide, sodium (bis)trimethylsilylamide and potassium (bis) trimethylsilylamide.

15. The process according to claim 9 wherein said silyl blocking group is trimethylsilyl.

16. The process according to claim 9 wherein said reducing step (2) is conducted in the presence of a borohydride reducing agent or a hydride reducing agent.

17. A diastereoselective process for producing a lactone of formula (5c) in a mixture of lactones of formula 5(c) and 5(d)

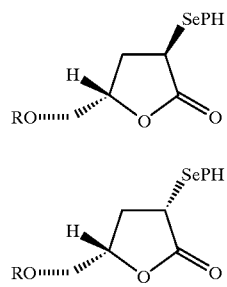
5(c)

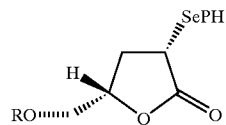
5(d)

where R is a hydroxyl protecting group (A) selected from the group consisting of t-butyldiphenylsilyl, triphenylsilyl, t-butyldimethylsilyl, trityl, methoxytrityl and pivaloyl comprising the steps of:

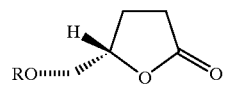
(4a)

with an effective amount of a strong base followed by introduction of a silyl blocking group (B) in a second step to produce a silyl-protected enol ether;

2) reacting the silyl-protected enol ether product obtained from step 1 with a phenyl-seleno compound of formula ArSeX where Ar is phenyl or a substituted phenyl and X is selected from the group consisting of $^-$OAc, $^-$OC(O)CF$_3$, $^-$SCN, $-$SO$_2$Ar, NR$_2$, and N-phthalimide, to produce the compound of formula 5c, said compound of formula 5c being produced in a proportion of at least about 90% by weight of said mixture of the compounds of formula 5c and 5d without further reaction.

18. The process according to claim 17 wherein said base is selected from the group consisting of butyl lithium, lithium diethylamide, lithium (bis)trimethylsilylamide, sodium (bis)trimethylsilylamide and potassium (bis)trimethylsilylamide.

19. The process according to claim 17 wherein said silyl blocking group (B) is a trimethylsilyl group.

* * * * *